United States Patent [19]

Sievert et al.

[11] Patent Number: 5,157,171

[45] Date of Patent: Oct. 20, 1992

[54] PROCESS FOR CHLOROFLUOROPROPANES

[75] Inventors: Allen C. Sievert, Elkton, Md.; Carl G. Krespan; Frank J. Weigert, both of Wilmington, Del.

[73] Assignee: E. I. Du Pont de Nemours and Company, Wilmington, Del.

[21] Appl. No.: 681,564

[22] Filed: Apr. 5, 1991

Related U.S. Application Data

[63] Continuation of Ser. No. 422,012, Oct. 16, 1989, abandoned.

[51] Int. Cl.$^5$ .................. C07C 17/28; C07C 17/00
[52] U.S. Cl. ............................ 570/151; 570/172; 570/175
[58] Field of Search ................... 570/172, 175, 151

[56] References Cited

U.S. PATENT DOCUMENTS

| | | | |
|---|---|---|---|
| 2,462,402 | 2/1949 | Joyce | 260/653 |
| 3,087,974 | 4/1963 | Hauptschein et al. | 260/653 |
| 3,398,202 | 8/1968 | Foulletier | 260/653 |
| 4,902,838 | 2/1990 | Manzer et al. | 570/151 |

FOREIGN PATENT DOCUMENTS 121710 10/1978 Japan.
78925 5/1985 Japan.
209824 8/1990 Japan.

OTHER PUBLICATIONS

Orchem RD-70-398, "Chlorofluorination I. Chlorofluorination of Propylene and Isopropylfluoride", D. M. Crouse (1970).
Paleta et al., Coll. Czech. Chem. Comm., vol. 35, pp. 1867-1875 (1971).
Coffman et al., The Journal of the American Chemical Society, vol. 71, pp. 979-980 (1949).

Primary Examiner—Howard T. Mars

[57] ABSTRACT

A process for the preparation of chlorofluoropropanes of the formula $C_3HCl_2F_5$ by contacting monofluorodichloromethane with tetrafluoroethylene in the presence of a modified aluminum chloride catalyst at a temperature of 0° to 150° C. The novel compound $CF_3CCl_2CHF_2$ is also disclosed.

11 Claims, No Drawings

PROCESS FOR CHLOROFLUOROPROPANES

This is a continuation of application Ser. No. 07/422,012, filed Oct. 16, 1989 now abandoned.

BACKGROUND OF THE INVENTION

1. Field of the Invention

This invention relates to a process for the preparation of chlorofluorocarbons and to a novel composition 2,2-dichloro-1,1,1,3,3-pentafluoropropane.

2. Background

For modern technological advances, particularly in the electric field, utmost cleanliness of the electronic components has become an important and necessary requirement. For example, in the manufacture of modern electronic circuit boards with increased circuitry and component densities, thorough and effective cleaning of the boards after soldering is of primary importance. Cleaning of electronic circuit boards is presently done for the most part by solvent washing utilizing various solvents and processes.

The solvent of choice at the present time is 1,1,2-trichloro-1,2,2-trifluoroethane (CFC-113) because this solvent provides the necessary characteristics required of an effective solvent such as convenient atmospheric boiling point, non-flammability, low toxicity, inertness to various materials of construction, high stability and high solvency. CFC-113 is often used with small amounts of co-solvent such as acetone or methanol to enhance certain solvency characteristics. CFC-113 and CFC-113-based solvents are also extensively used in cleaning of precision machine parts. In recent years, however, CFC-113 has been suspected of contributing to the depletion of the stratospheric ozone layer. Because of its unusually high stability, it is believed that CFC-113 remains intact in the earth's atmosphere until it reaches the stratosphere and there undergoes decomposition, the decomposition product bringing about the destruction of the ozone layer.

It is, therefore, obvious that there is an urgent need in the industry for a solvent to replace CFC-113 which will provide the beneficial solvent characteristics of CFC-113, but at the same time have little or no stratospheric ozone depletion potential.

It is an object of the present invention to provide an effective chlorofluorocarbon solvent system. It is a further object of the invention to provide an effective chlorofluorocarbon solvent system which has little or no effect upon the stratospheric ozone layer. It is still a further object of the present invention to provide an improved process for the manufacture of chlorofluoropropanes.

SUMMARY OF THE INVENTION

This invention provides a process for the preparation of hydrogen-containing chlorofluoropropanes represented by the formula $C_3HCl_2F_5$, said process comprising contacting monofluorodichloromethane with tetrafluoroethylene in the presence of a modified aluminum chloride catalyst at a temperature of from about 0° C. to about 150° C. and recovering hydrogen-containing chlorofluoropropanes. Said modified aluminum chloride being prepared by contacting anhydrous aluminum chloride with chlorofluorocarbon of 1 to 2 carbon atoms and removing liquid products therefrom. This invention also provides a novel compound 2,2-dichloro-1,1,1,3,3-pentafluoropropane.

DETAILED DESCRIPTION OF THE INVENTION

A solvent system which will be used as a replacement for CFC-113 should have characteristics very similar to those of CFC-113 such as relatively low atmospheric boiling point (CFC-113 boils at approximately 47° C.), non-flammability, low toxicity, inertness to various materials of construction, high solvency, and in-use stability. For the replacement solvent to have little or no effect upon the ozone depletion process, the solvent must have stability characteristics somewhat different from that of CFC-113. The solvent should be sufficiently stable to be used effectively in various cleaning processes, but should be unstable enough to completely or almost completely decompose in the troposphere so that little or none will survive to reach the stratosphere.

It is generally believed by those skilled in the art that such stability characteristics can be achieved for the most part by hydrogen-containing chlorofluorocarbons (HCFC's). The rationale being that such hydrogen-containing chlorofluorocarbons now undergo dehydrohalogenation, such as dehydrochlorination, in the atmosphere such that the compounds do not survive to reach the stratosphere.

It has now been found that certain hydrogen-containing chlorofluorocarbon derivatives of propane represented by the formula $C_3HCl_2F_5$ have the necessary characteristics discussed above. Thus in terms of atmospheric boiling points, the presently known isomeric $C_3HCl_2F_5$ are reported to have boiling points fairly close to that of CFC-113, i.e., in the range of from about 50° C. to about 56° C. Thus, $CHClFCCIFCF_3$ (I) boils at 56° C., $CHF_2CCIFCCIF_2$ (II) boils at 56.3° C., $CHCl_2CF_2CF_3$ (III) boils at 53.0° C., $CHCIFCF_2CClF_2$ (IV) boils at 52.0° C., and $CClF_2CHClCF_3$ (V) boils at 50.4° C. Boiling points reasonably close to that of CFC-113 are desirable so that presently used solvent cleaning systems and processes can be used without too much modification.

While the above-disclosed hydrochlorofluoropropanes are known and should be useful in solvent cleaning system, there is no satisfactory process for preparing them, particularly in large quantities required for industrial uses.

At present, a great majority of chlorofluorocarbons and hydrochlorofluorocarbons, particularly those produced in large quantities, are manufactured by processes involving halogen exchange reactions, i.e., replacing one or more chlorine atoms of a halocarbon by a fluorine atoms(s) either by the reaction with a fluorinating agent such as antimony chlorofluorides and the like, or by the reaction of the halocarbon with hydrogen fluoride in the presence of a fluorination catalyst such as antimony halide, chromium oxide, aluminum fluoride and the like. Such processes involve at least the steps of preparing the required chlorocarbons and then carrying out the fluorine exchange reaction on the chlorocarbons. The preparation of chlorocarbons or hydrogen-containing chlorocarbons generally proceed reasonably well with one or two carbon compounds; however, with three carbon atom compounds, i.e., the propane series, both the preparation of the suitable chloropropanes and the subsequent halogen exchange reactions proceed with great difficulty and usually in unsatisfactory low yields.

In accordance with the present invention, it has now been found that certain isomeric hydrogen-containing chlorofluoropropanes of the formula $C_3HCl_2F_5$ can be prepared readily in good yields by the reaction of monofluorodichloromethane with tetrafluoroethylene in the presence of a modified aluminum chloride catalyst. The reaction may be represented by equation (1).

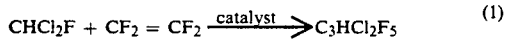

(1)

"$C_3HCl_2F_5$" in equation (1) represents an isomeric mixture of hydrogen-containing chlorofluoropropanes. The reaction of $CHCl_2F$ with $CF_2=CF_2$ to produce hydrogen-containing chlorofluoropropanes has been disclosed by Joyce in U.S. Pat. No. 2,462,402 and by Coffman, et. al. in *The Journal of the American Chemical Society*, Vol. 71, pages 979-980 (1949) wherein the catalyst used was ordinary aluminum chloride. The disadvantage of the process as disclosed above using ordinary aluminum chloride as the catalyst, is the extensive halogen exchange reaction which takes place. At least one aspect of such exchange is the production of a fairly large amount of chloroform ($CHCl_3$) from $CHCl_2F$ which means considerable loss of valuable reactant. The other disadvantage arising from extensive halogen exchange is that in this particular reaction the chloroform produced forms azeotropes with most of the $C_3HCl_2F_5$ isomers which makes recovery of $C_3HCl_2F_5$ by conventional industrial means, e.g., distillation, difficult and expensive.

It has now been found that the above-described reaction (1) can be carried out providing higher yields of desired hydrogen-containing chlorofluoropropanes and surprisingly with little or no conversion of the monofluorodichloromethane to chloroform when said reaction is carried out using a modified aluminum chloride catalyst, to be described below, in place of the art-taught ordinary aluminum chloride.

Above-cited Joyce and Coffman, et. al. references describe the hydrogen-containing chlorofluoropropane product as 1,3-dichloro1,2,2,3,3-pentafluoropropane, i.e., $CHClFCF_2CClF_2$; however, Paleta, et. al. in Coll. Czech. Chem. Comm. Vol. 35, page 1867–1875 (1971) reported that the chlorofluoropropane products actually obtained were an isomeric mixture consisting of about 41% 1,3-dichloro-1,2,2,3,3-pentafluoropropane, $CHClFCF_2CClF_2$, and about 59% 1,1-dichloro-2,2,3,3,3-pentafluoropropane, $CHCl_2CF_2CF_3$.

Applicants have now found that by using the modified aluminum chloride catalyst instead of ordinary aluminum chloride, not only are higher yields of hydrogen-containing chlorofluoropropanes obtained, and the formation of chloroform from monofluorodichloromethane either eliminated or greatly reduced, but a heretofore unknown isomeric hydrogen-containing chlorofluoropropane, i.e., 2,2-dichloro-1,1,3,3,3-pentafluoropropane, $CHF_2CCl_2CF_3$, is also obtained in appreciable quantities.

This new isomeric dichloropentafluoropropane, $CHF_2CCl_2CF_3$, should be particularly desirable from structural considerations since the hydrogen atom is located on one of the terminal carbon atoms of the propane molecule and both chlorine atoms are located on the middle carbon atom. Such structure should insure greater ease of dehydrochlorination in the atmosphere so that none of the compound should survive to reach the stratosphere and participate in the ozone depletion process. This isomer may also be less toxic than the other isomers.

On the other hand it is important that cleaning compositions possess adequate stability under use conditions. Dehydrochlorination is known in the art to be typically more facile than dehydrofluorination. Loss of hydrogen halides under use conditions is undesirable since it can result in corrosion of metal parts. The new $CHF_2CCl_2CF_3$ isomer appears to have adequate stability under mild conditions as indicated by the reactivity of a mixture of three $C_3HCl_2F_5$ isomers —$CHCl_2CF_2CF_3$, $CHClFCF_2CClF_2$, and $CHF_2CCl_2CF_3$— with aqueous NaOH, see Example 10. The isomer distribution before and after the reaction with NaOH indicated that the $CHCl_2CF_2CF_3$ isomer was the least stable of the three isomers under these conditions.

The claimed reaction process is carried out by contacting monofluorodichloromethane with tetrafluoroethylene in the presence of a modified aluminum chloride catalyst in the temperature range of from about 0° C. to about 150° C.

The modified aluminum chloride catalysts used in the process of the invention are prepared by treating anhydrous aluminum chloride with an excess of chlorofluorocarbons, hydrochlorofluorocarbons, or hydrofluorocarbons such as $CH_3F$, $CH_2F_2$, $CHF_3$, $CCl_2FCCl_3$, $CClF_2CCl_3$, $CF_3CCl_3$, $CF_3CCl_2F$, $CF_3CClF_2$, $CHCl_2CCl_2F$, $CHClFCCl_3$, $CHCl_2CClF_2$, $CHClFCCl_2F$, $CHF_2CCl_3$, $CHCl_2CF_3$, $CHClFCClF_2$, $CHF_2CCl_2F$, $CHClFCF_3$, $CHF_2CClF_2$, $C_2HF_5$, $CHClFCHCl_2$, $CH_2ClCCl_2F$, $CH_2FCCl_3$, $CHClFCHClF$, $CHCl_2CHF_2$, $CH_2ClCClF_2$, $CH_2FCCl_2F$, $CHClFCHF_2$, $CH_2ClCF_3$, $CH_2FCClF_2$, $CHF_2CHF_2$, $CH_2FCF_3$, $CH_2ClCHClF$, $CH_2FCHCl_2$, $CH_3CCl_2F$, $CH_2ClCHF_2$, $CH_2FCHClF$, $CH_3CClF_2$, $CH_2FCHF_2$, $CH_3CF_3$, $CH_2FCH_2Cl$, $CH_3CHClF$, $CH_2FCH_2F$, $CH_3CHF_2$, and $C_2H_5F$; preferably $CCl_2F_2$, $CHCl_2F$, $CHClF_2$, $CH_2ClF$, $CCl_2FCCl_2F$, $CCl_2FCClF_2$, $CClF_2CClF_2$; and most preferably $CCl_3F$. Propane derivatives displaying the structural features shown above may also be used in the process of this invention. The reaction between aluminum chloride and the chlorofluorocarbons, hydrochlorofluorocarbons, or hydrofluorocarbons occurs, for the most part, spontaneously and is exothermic. In certain instances, such as with $C_2$ chlorofluorocarbons, slight heating may be used advantageously. For compounds containing —$CF_3$ groups such as $CHF_3$, $CCl_3CF_3$, $CHCl_2CF_3$, $CH_2ClCF_3$, and $CH_3CF_3$ more vigorous conditions are required to effect reaction with $AlCl_3$, and the reaction is best carried out under the pressure developed autogenously by the reactants.

After the reaction has subsided, the liquid products are removed, generally under reduced pressures to provide a modified aluminum chloride catalyst which will usually contain from about 3 to about 68% fluorine. The liquid product from the reaction of chlorofluorocarbons with $AlCl_3$ includes products which are produced by halogen exchange reaction with the aluminum chloride as well as rearranged chlorofluorocarbons. Thus, when $CCl_3F$ is used to modify the aluminum chloride, the halogen exchange product will be $CCl_4$, and when $CHCl_2F$ is used, the product is $CHCl_3$. When $CCl_2FCClF_2$ is used to modify the aluminum chloride, the liquid products of the reaction include $CCl_3CF_3$, $CCl_3CClF_2$, and $C_2Cl_6$.

The solid modified aluminum chloride product of the reaction of $AlCl_3$ with chlorofluorocarbons may be separated from the liquid products by filtration, by distillation or vacuum transfer of the liquid products from the modified aluminum chloride, or, alternatively, the modified aluminum chloride catalyst may be used as a suspension for subsequent reactions.

Since the instant process involves the addition of one mole of monofluorodichloromethane to one mole of tetrafluoroethylene as indicated by equation (1), the appropriate molar ratio of the reactants should be 1:1 although a slight excess of either reactant may be used if desired. A large excess of monofluorodichloromethane could result in chloroform formation despite the use of modified aluminum chloride catalyst and should be avoided. A large excess of tetrafluoroethylene, while not harmful, serves no useful purpose. Both reactants, $CHCl_2F$ and $CF_2=CF_2$, are articles of commerce and are readily available. The tetrafluoroethylene used in the process of the invention may be optionally inhibited with d-limonene to reduce the possibility of initiating a hazardous polymerization.

The present invention process can be carried out either batch-wise or in a continuous fashion. In the continuous process, a mixture of monofluorodichloromethane and tetrafluoroethylene is passed through or over a bed of modified aluminum chloride at suitable temperature and pressure and the desired products recovered from the effluent by conventional means such as fractional distillation.

In the batch process all of the reactants may be combined together in the reactor. Alternatively, the reactor may be initially charged with catalyst and tetrafluoroethylene, and the dichlorofluoromethane metered into the reactor at the desired rate. If the reactor is charged with catalyst and $CHCl_2F$, it is important that the reaction be kept cold to minimize the disproportionation of $CHCl_2F$ to chloroform which can occur even with the modified aluminum chloride catalyst under favorable circumstances.

The process of the invention may be run with or without a solvent. If a solvent is used it must be one which will not react with the modified aluminum chloride catalyst and have a boiling point appropriate for eventual separation of the $C_3HCl_2F_5$ isomeric mixture. Solvents that can be used for the process of the invention include unreactive chlorocarbons, such as $CH_2Cl_2$, or unreactive chlorofluorocarbons, such as $CF_3CCl_2CF_3$. A preferred solvent is $CHCl_2CF_3$; the most preferred solvent is the product, the $C_3HCl_2F_5$ isomeric mixture or any of the individual isomers.

The reaction temperature may be varied widely in the range of from about 0° C. to about 150° C. The preferred temperature range is from about 10° C. to about 100° C. The most preferred range is from about 25° C. to 70° C.

Pressure likewise may be varied widely from subatmospheric to superatmospheric, but preferably the reaction is carried out at somewhat elevated pressures, particularly at pressures generated autogenously in conformity with the reaction temperature employed. The pressure of the reaction may be controlled by adjusting the amount of unreacted $CHCl_2F$ and $CF_2=CF_2$ present in the reactor.

The reaction time, or time necessary for sufficient completion of the reaction, is somewhat dependent on the temperature chosen for the reaction, but the completion of the reaction is easily determined by the change in the pressure in the reaction vessel. Thus, if the reaction were being carried out at a given temperature under autogenous pressure, the pressure will continue to drop as the reaction proceeds and the time at which the pressure stops decreasing is taken as the end of the reaction period. Generally, the reaction time is in the range of from about 0.25 hours to about 3 hours at the preferred temperature range.

The amount of modified aluminum chloride to be used, i.e., the catalytic amount, will be from about 1 to about 20 percent based on the reactant weight, preferably from about 3 to about 12 percent.

The products of the present process may be recovered by any conventional means such as by filtration or by distillation either before or after decompostion of the modified aluminum chloride by water.

In some embodiments it may be desirable to enrich the $CF_3CCl_2CHF_2$ content of the reaction mixture prior to recovery. This can be accomplished by isomerization using an alumina catalyst. In this process the reaction product is passed over a halide modified alumina catalyst at temperatures of 200° to 400° C. as further described in Example 4.

The composition of $C_3HCl_2F_5$ mixture may also be enriched in the $CHF_2CCl_2CF_3$ component by isomerization in the liquid phase using the modified aluminum chloride catalyst prepared as described above. In this case the isomerization can be carried out by heating the mixture of the $C_3HCl_2F_5$ isomers and the aluminum chloride catalyst at temperatures of 50° to 200° C. under the pressure developed autogenously by the sample. The preferred catalyst is the $CCl_3F$-modified aluminum chloride. This procedure is further described in Example 5.

The halide modified alumina catalysts suitable for isomerization of mixtures of dichloropentafluoropropanes to enrich the 1,1,1,3,3-pentafluoro-2,2-dichloropropane content of such mixtures may be prepared in the following manner.

A quantity of alumina having a surface area greater than 100 m²/g is dried until essentially all moisture is removed, e.g., for about 18 hours at 100° C. The dried catalyst is then transferred to the reactor to be used.

The alumina catalysts can be fluorided prior to the isomerization by treatment with a vaporizable fluorine-containing fluorinating compound, such as HF, $CCl_3F$, $CCl_2CF_2$, $CHF_3$, or $CCl_2FCClF_2$, at elevated temperatures until the desired degree of fluorination is obtained, e.g., at about 200° C. to about 450° C. By vaporizable fluorine-containing compound is meant a compound which will convert the alumina component of the catalyst to the desired degree of fluorination using pretreatment conditions which are well known to the art. The treatment with HF or other vaporizable fluorine-containing compound can conveniently be done in the reactor which is to be used for the isomerization reactions.

EXAMPLES

Example 1

Preparation of $CCl_3F$ Modified Aluminum Chloride

A 500 mL three neck round bottom flask was charged with 50 g (0.375 mole) of $AlCl_3$. The flask was passed out of the dry box and fitted with an addition funnel and a dry ice condenser topped with a nitrogen bubbler. The addition funnel was charged with 175 mL of $CCl_3F$ (CFC-11) and the condenser was filled with a methanol/dry ice mixture. The CFC-11 was gradually added to the flask and the mixture began to reflux vigorously. The reaction continued to reflux for an hour after all of the CFC-11 had been added. The reaction was not heated. GC analysis of the supernatant liquid indicated it was virtually pure $CCl_4$. The volatiles were removed in vacuum and the resulting solid dried in vacuum to afford 31 g of tan powder. Analysis: Al, 28.1% (by weight).

Example 2

Preferred Mode of the Invention

CFC-11 modified aluminum chloride (13.3 g; prepared as in Example 1) was placed in a 400 mL "Hastelloy" C nickel alloy bomb. The bomb was sealed, cooled to $-78°$ C., and purged with nitrogen three times. The bomb was evacuated once again and $CHCl_2F$ (51.5 g, 0.50 mole) was condensed into it. The bomb was then placed in a barricade and agitated by shaking. Uninhibited tetrafluoroethylene (50 g, 0.50 mole) from a pressurized cylinder resting on a balance was added to the bomb via a remote valve. The temperature of the bomb was raised to $40°$ C. and held at that temperature for 8 h. During this time the pressure in the bomb rose to 63 psig and gradually decreased to 35 psig. The bomb was then cooled, vented, purged and the contents poured into a jar. The crude product, weighing 111 g, consisted of a yellow supernatant over a brown gelatinous solid. The product was quenched in water and the organic layer dried over anhydrous sodium sulfate affording 65.65 g of product. Analysis of the organic layer by $^1H$ NMR indicated that the following compounds were present (mole percent): 58% $CHCl_2CF_2CF_3$, 23% $CHF_2CCl_2CF_3$, 5% $CHClFCF_2CClF_2$, and 7% $CHCl_2CF_2CClF_2$; no chloroform was detected.

Example 3

This example shows that the reaction can be run at higher temperature without substantially affecting the results.

Following a procedure similar to that of Example 2, CFC-11 modified aluminum chloride (6.7 g) and $CHCl_2F$ (51.5 g, 0.50 mole) were reacted with tetrafluoroethylene (50 g, 0.50 mole). The reaction was held at $68°-72°$ C. for 3 hours. During this time, the pressure in the bomb rose to 83 psig, and then gradually dropped to 68 psig. Analysis of the product by $^1H$ NMR indicated that the following compounds were present (mole percent): 63% $CHCl_2CF_2CF_3$, 24% $CHF_2CCl_2CF_3$, 5% $CHClFCF_2CClF_2$, 6% $CHCl_2CF_2CClF_2$, and 2% $CHCl_2CCl_2CF_3$; no chloroform was detected.

Comparative Example 1

The literature does not report $CHF_2CCl_2CF_3$ (HCFC 225aa) as a product from $CHCl_2F$ and tetrafluoroethylene. The following example confirms that HCFC 225aa is not formed under literature conditions.

The reaction was carried out with a substantial excess of dichlorofluoromethane in the manner described by Paleta O.; Posta, A.; Tesarik, K., Coll. Czech. Chem. Comm., 1971, 36 (5). 1967.

A 240-mL "Hastelloy" C nickel alloy tube was charged with 5.0 g of aluminum chloride, 90 g (0.87 mol) of dichlorofluoromethane, and 30 g (0.30 mol) of tetrafluoroethylene, then agitated at about $25°$ C. for 3 hrs. Volatile liquids, 86.4 g were transferred under vacuum from the crude reaction mixture. GC analysis showed 44.7% of the mixture, or 38.6 g (63% yield), to be the expected products, 1,1-dichloro-2,2,3,3,3-pentafluoropropane and 1,3-dichloro-1,1,2,2,3-pentafluoropropane in 75:25 ratio.

Considerable chloroform (22%) was also formed, so the mixture was fractionated in an attempt to isolate the pure propane isomers. Fractions having a boiling point range of $41°-60°$ C. were collected, and selected cuts representing the range of compositions were analyzed by NMR. The $^1H$ and $^{19}F$ NMR spectra confirmed the identities of the two products and also showed that 2,2-dichloro-1,1,1,3,3-pentafluoropropane was not present.

Example 4

Preparation of a $C_3HCl_2F_5$ Mixture Enriched in $CHF_2CCl_2CF_3$ by Isomerization A liquid mixture of HCFC-225 isomers containing 66 mol% $CHCl_2CF_2CF_3$ (HCFC-225ca), 29 mol% $CHClFCF_2CClF_2$ (HCFC-225cb), 5 mol% $CHF_2CCl_2CF_3$ (HCFC-225aa) and <1 mol% $CHClFCClFCF_3$ (HCFC-225ba) was passed over an alumina catalyst (Harshaw Al-3945, 4 g) in a glass tube at the rate of 1 mL/h along with nitrogen carrier gas (5 sccm). The liquid product was condensed at $-78°$ C. and analyzed by gas chromatography and $^{19}F$ NMR. At $380°$ C. the composition of the product was 70, mol% HCFC-225ca, <1 mol% HCFC-225cb, 25 mol% HCFC-225aa and 4 mol% HCFC-225ba. It is seen that the concentration of HCFC-225aa has been increased five-fold.

Example 5

Preparation of an $C_3HCl_2F_5$ Isomer Mixture Enriched in $CHF_2CCl_2CF_3$ by Isomerization in the Liquid Phase A 400 mL Hastelloy ® nickel alloy shaker tube was charged with 33 g of a mixture of $C_3HCl_2F_5$ isomers (composition of the sample below) and 6.7 g of CFC-11-modified aluminum chloride. The tube was cooled to $-78°$ C., evacuated, and purged with nitrogen. The evacuated tube was placed in the barricade and heated to $150°-161°$ C. for 8 h; pressure was 130 psig. The tube was then cooled, vented, purged with nitrogen and the product poured into a jar. The product consisted of a yellow supernatant over a brown solid. The supernatant was analyzed by GC and $^1H$ NMR. The composition of the sample was as indicated below. The analyses indicate that a substantial amount of the $CHClFCF_2CClF_2$ isomer was converted to the $CHF_2CCl_2CF_3$ isomer under these conditions. In addition there was some conversion of the $C_3HCl_2F_5$ isomers to $C_3HCl_3F_4$ and $C_3HCl_4F_3$ isomers.

| Compound | Composition Mole % | |
|---|---|---|
| | Starting Material | Product |
| $CHCl_2CF_2F_3$ | 65.0 | 61.7 |
| $CHF_2CCl_2CF_3$ | 14.1 | 22.0 |
| $CHClFCF_2CClF_2$ | 16.9 | 8.9 |
| $CHCl_2F$ | 0.9 | — |
| $CHCl_3$ | 1.0 | 1.4 |
| $C_3HCl_3F_4$'s | 2.0* | 4.3* |
| $CHCl_2CCl_2CF_3$ | — | 1.8 |

*Estimated

Example 6

This example shows that the amount of catalyst can be increased without substantially changing the outcome of the reaction.

Following a procedure similar to that of Example 2, CFC-11 modified aluminum chloride (13.3 g) and CHCl$_2$F (51.5 g, 0.50 mole) were reacted with tetrafluoroethylene (50 g, 0.50 mole). The reaction was held at 40° C. for 3 hours. Analysis of the product by $^1$H NMR indicated that the following compounds were present: 63% CHCl$_2$CF$_2$CF$_3$, 24% CHF$_2$CCl$_2$CF$_3$, 4% CHClFCF$_2$CClF$_2$, 7% CHCl$_2$CF$_2$CClF$_2$, 2% CHCl$_2$CCl$_2$CF$_3$; no chloroform was detected.

Example 7

Preparation of CHCl$_2$F Modified Aluminum Chloride

Reagent grade aluminum chloride (50 g, 0.37 mole) suspended in 100 mL of chloroform was stirred while 203 g (2.0 mole) of dichlorofluoromethane was distilled in over a two hour period. Moderate cooling was used to keep the temperature below 32° C. Removal of volatiles under vacuum left 33.8 g of tan solid which was stored in a dry box. Analysis: 64.5% F (by weight).

Example 8

This example demonstrates the use of CHCl$_2$F modified AlCl$_3$ as a catalyst for the reaction of tetrafluoroethylene with CHCl$_2$F.

A 240 mL "Hastelloy" C nickel alloy bomb was charged with CHCl$_2$F modified aluminum chloride (5.0 g). The bomb was evacuated and CHCl$_2$F (52 g, 0.50 mole), and tetrafluoroethylene (50 g, 0.50 mole) were condensed into the bomb. The bomb was agitated at 25° C. for 8 hours. The crude reaction product was filtered into a cooled receiver to afford 59.6 g of product. This material was shown by GC analysis to contain 19% CHCl$_2$CF$_2$CClF$_2$ and 77% of C$_3$HCl$_2$F$_5$ isomers; no chloroform was detected. Fractionation of the sample afforded 43.4 g of C$_3$HCl$_2$F$_5$ isomers which were analyzed by $^1$H and $^{19}$F NMR and shown to consist of 67% CHCl$_2$CF$_2$CF$_3$, 22% CHF$_2$CCl$_2$CF$_3$, and 11% CHClFCF$_2$CClF$_2$.

Example 9

Preparation of CCl$_2$FCClF$_2$ (CFC-113) Modified Aluminum Chloride

A 500 mL three neck round bottom flask fitted with a mechanical stirrer, a dropping funnel, and a 12° C. reflux condenser topped with a nitrogen bubbler was charged with 44.4 g (0.333 mole) of reagent grade AlCl$_3$. CFC-113 (250 mL) was added to the addition funnel and also (50 mL) to the stirred AlCl$_3$; the remainder of the CFC-113 was then added rapidly. The reaction was refluxed for 1.25 h. The reaction supernatant was found to contain CF$_3$CCl$_3$ (CFC-113a), CCl$_3$CClF$_2$ (CFC-112a), and hexachloroethane by GC and GC-LS analysis. The volatile products were removed in vacuum to afford 57.3 g of yellow powder. This material contained 13.6% Al by weight and was obviously contaminated with organic products probably CCl$_3$CCl$_2$F (CFC-111) and hexachloroethane.

Example 10

This example demonstrates the use of CFC-113 modified aluminum chloride as the catalyst for the reaction of tetrafluoroethylene with CHCl$_2$F %.

Following a procedure similar to that of Example 2, CFC-113 modified aluminum chloride (13.3 g; prepared as in Example 8), CHCl$_2$F (51.5 g, 0.50 mole), and tetrafluoroethylene (50 g, 0.50 mole) were reacted at 40° C. for 3 hours. During this time, the pressure in the bomb rose to 192 psig, and then gradually dropped to 158 psig. Analysis of the product by $^1$H NMR indicated that the following compounds were present: 47% CHCl$_2$CF$_2$CF$_3$, 7% CHF$_2$CCl$_2$CF$_3$, 22% CHClFCF$_2$CClF$_2$, 18% CHCl$_2$CF$_2$CClF$_2$, 4% CHCl$_2$CCl$_2$CF$_3$, 1% 1,1,2,2,3,3,3-heptachloropropane, and 0.3% chloroform.

Example 11

Reaction of C$_3$HCl$_2$F$_5$ Isomers with NaOH

A mixture of C$_3$HCl$_2$F$_5$ isomers (5 mL) was treated with 10 mL of 10% aqueous NaOH and the resulting two-phase mixture refluxed for 45 hours. The initial and final composition of the C$_3$HCl$_2$F$_5$ mixture is indicated in the Table below. An additional compound was observed in the final solution; this was identified by $^{19}$F NMR as CCl$_2$=CFCF$_3$ arising from dehydrofluorination of CHCl$_2$CF$_2$CF$_3$.

| Initial C$_3$HCl$_2$F$_5$ Composition | | Final C$_3$HCl$_2$F$_5$ Composition | |
| --- | --- | --- | --- |
| Isomer | % | Isomer | % |
| CHCl$_2$CF$_2$CF$_3$ | 65 | CHCl$_2$CF$_2$CF$_3$ | 50 |
| CHF$_2$CCl$_2$CF$_3$ | 18 | CHF$_2$CCl$_2$CF$_3$ | 24 |
| CHClFCF$_2$CClF$_2$ | 18 | CHClFCF$_2$CClF$_2$ | 26 |

Example 12

Reaction of CHCl$_2$F with Tetrafluoroethylene in HCFC-123

CFC-11-modified aluminum chloride (13.3 g) and HCFC-123 (60 g, 0.40 mole) was placed in a 400 mL "Hastelloy" C shaker tube. The tube was sealed and cooled to −78° C. in a dry ice-acetone bath, and then alternately evacuated and purged with nitrogen three times. The tube was evacuated once again and CHCl$_2$F (103 g, 1.0 mole) was condensed into it. The tube bomb was then placed in the barricade and agitation begun. Uninhibited tetrafluoroethylene (19 g, 0.19 mole) was added to the bomb via a remote valve attached to a pressurized working cylinder resting on a balance. The temperature of the bomb was raised to 30° C. and the pressure increased to about 120 psig over the course of about 1 hour. After about 1.5 hours of reaction time (temperature, 34° C.; pressure, 125 psig), an additional 10 g of TFE were added to the bomb. A heat kick of approximately 8° C. was observed and the pressure in the bomb dropped from 134 psig to 117 psig within 15 minutes. Additional TFE was added to the bomb in 4–11 g portions over the course of the next 1.8 hours. A total of 100 g TFE had been added at this point and the pressure in the bomb decreased to 93 psig (temperature, 45° C.). The temperature was held at 41°–45° C. for 3 hours.

The bomb was then cooled, vented, purged, and the contents poured into a jar. The product consisted of a clear supernatant over a viscous, brown lower layer. The crude reaction product weighed 251 g; this corresponded to a weight increase of about 177 g. $^1$H NMR analysis of the supernatant indicated the following composition (mole %): CHCl$_2$CF$_3$, 26%; CHCl$_2$CF$_2$CF$_3$, 42%; CHF$_2$CCl$_2$CF$_3$, 8%; CHClFCF$_2$CClF$_2$, 16%; CHCl$_2$CF$_2$CClF$_2$, 6%; CHCl$_2$CCl$_2$CF$_3$, 2%. No chloroform was detected by GC or $^1$H NMR.

We claim:

1. A process for enriching the $CF_3CCl_2CHF_2$ content of a mixture of chlorofluoropropanes of the nominal formula $C_3HCl_2F_5$ comprising contacting the mixture with a fluoride modified alumina isomerization catalyst at temperatures between 200° to 400° C.

2. The process of claim 1 wherein the fluoride modified alumina isomerization catalyst is prepared by treating anhydrous alumina with HF, $CCl_3F$, $CCl_2CF_2$, $CHF_3$, or $CCl_2FCClF_2$ at temperatures from 200° C. to 450° C.

3. A process for enriching the $CF_3CCl_2CHF_2$ content of an initial mixture of chlorofluoropropanes of the nominal formula $C_3HCl_2F_5$ comprising the steps of: modifying anhydrous aluminum chloride prior to any contact thereof with said initial mixture, by treating said aluminum chloride with an excess of $CH_3F$, $CH_2F_2$, $CHF_3$, $CCl_2FCCl_3$, $CClF_2CCl_3$, $CF_3CCl_3$, $CF_3CCl_2F$, $CF_3CClF_2$, $CHCl_2CCl_2F$, $CHClFCCl_3$, $CHCl_2CClF_2$, $CHClFCCl_2F$, $CHF_2CCl_3$, $CHCl_2CF_3$, $CHClFCClF_2$, $CHF_2CCl_2F$, $CHClFCF_3$, $CHF_2CClF_2$, $C_2HF_5$, $CHClFCHCl_2$, $CH_2ClCCl_2F$, $CH_2FCCl_3$, $CHClFCHClF$, $CHCl_2CHF_2$, $CH_2ClCClF_2$, $CH_2FCCl_2F$, $CHClFCHF_2$, $CH_2ClCF_3$, $CH_2FCClF_2$, $CHF_2CHF_2$, $CH_2FCF_3$, $CH_2ClCHClF$, $CH_2FCHCl_2$, $CH_3CCl_2F$, $CH_2ClCHF_2$, $CH_2FCHClF$, $CH_3CClF_2$, $CH_2FCHF_2$, $CH_3CF_3$, $CH_2FCH_2Cl$, $CH_3CHClF$, $CH_2FCH_2F$, $CH_3CHF_2$, $C_2H_5F$, $CCl_2F_2$, $CHCl_2F$, $CHClF_2$, $CH_2ClF$, $CCl_2FCCl_2F$, $CCl_2FCClF_2$, $CClF_2CClF_2$, or $CCl_3F$ to provide a catalyst containing from 3% to 68% by weight fluorine; and thereafter contacting said initial mixture with the modified aluminum chloride catalyst at a temperature within the range of from 50° C. to 200° C. under autogenous pressure.

4. A process for the preparation of a product containing the compound $CF_3CCl_2CHF_2$ comprising the steps of: modifying anhydrous aluminum chloride prior to its contact with a reaction mixture comprising both monofluorodichloroethane and tetrafluoroethylene by treating said aluminum chloride with an excess of $CH_3F$, $CH_2F_2$, $CHF_3$, $CCl_2FCCl_3$, $CClF_2CCl_3$, $CF_3CCl_3$, $CF_3CCl_2F$, $CF_3CClF_2$, $CHCl_2CCl_2F$, $CHClFCCl_3$, $CHCl_2CClF_2$, $CHClFCCl_2F$, $CHF_2CCl_3$, $CHCl_2CF_3$, $CHClFCClF_2$, $CHF_2CCl_2F$, $CHClFCF_3$, $CHF_2CClF_2$, $C_2HF_5$, $CHClFCHCl_2$, $CH_2ClCCl_2F$, $CH_2FCCl_3$, $CHClFCHClF$, $CHCl_2CHF_2$, $CH_2ClCClF_2$, $CH_2FCCl_2F$, $CHClFCHF_2$, $CH_2ClCF_3$, $CH_2FCClF_2$, $CHF_2CHF_2$, $CH_2FCF_3$, $CH_2ClCHClF$, $CH_2FCHCl_2$, $CH_3CCl_2F$, $CH_2ClCHF_2$, $CH_2FCHClF$, $CH_3CClF_2$, $CH_2FCHF_2$, $CH_3CF_3$, $CH_2FCH_2Cl$, $CH_3CHClF$, $CH_2FCH_2F$, $CH_3CHF_2$, $C_2H_5F$, $CCl_2F_2$, $CHCl_2F$, $CHClF_2$, $CH_2ClF$, $CCl_2FCCl_2F$, $CCl_2FCClF_2$, $CClF_2CClF_2$, or $CCl_3F$ to provide a catalyst containing from 3% to 68% by weight fluorine; and thereafter reacting in the presence of a catalytic amount of the modified aluminum chloride catalyst monofluorodichloromethane with tetrafluoroethylene at a temperature within the range of from 0° C. to 150° C. for a time sufficient to produce a reaction product that contains the compound $CF_3CCl_2CHF_2$.

5. The process of claim 4 wherein the anyhydrous aluminum chloride is modified to provide a reaction product which is essentially free from chloroform.

6. The process of claim 4 wherein chlorofluorocarbon is selected from $CCl_3F$, $CCl_2F_2$, $CHCl_2F$, $CHClF_2$, $CH_2ClF$, $CCl_2FCCl_2F$, $CCl_2FCClF_2$ and $CClF_2CClF_2$.

7. The process of claim 4 wherein the chlorofluorocarbon is $CCl_3F$.

8. The process of claim 4 wherein the chlorofluorocarbon is $CHCl_2F$.

9. The process of claim 4 conducted in the presence of an inert solvent.

10. The process of claim 8 wherein the solvent is $C_3HCl_2F_5$ or $CF_3CHCl_2$.

11. The process of claim 4 wherein the $CF_3CCl_2CHF_2$ is recovered from the reaction product.

* * * * *